US009721780B2

(12) United States Patent
Richardson

(10) Patent No.: US 9,721,780 B2
(45) Date of Patent: *Aug. 1, 2017

(54) M/Z TARGETED ATTENUATION ON TIME OF FLIGHT INSTRUMENTS

(71) Applicant: Micromass UK Limited, Wilmslow (GB)

(72) Inventor: Keith Richardson, Derbyshire (GB)

(73) Assignee: Micromass UK Limited, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/847,574

(22) Filed: Sep. 8, 2015

(65) Prior Publication Data
US 2015/0380230 A1  Dec. 31, 2015

Related U.S. Application Data

(63) Continuation of application No. 14/004,963, filed as application No. PCT/GB2012/050576 on Mar. 15, 2012, now Pat. No. 9,129,781.

(60) Provisional application No. 61/452,772, filed on Mar. 15, 2011.

(30) Foreign Application Priority Data

Mar. 15, 2011 (GB) .................................. 1104292.6

(51) Int. Cl.
H01J 49/26 (2006.01)
H01J 49/40 (2006.01)
H01J 49/00 (2006.01)

(52) U.S. Cl.
CPC .......... *H01J 49/401* (2013.01); *H01J 49/004* (2013.01); *H01J 49/0027* (2013.01); *H01J 49/0031* (2013.01); *H01J 49/40* (2013.01)

(58) Field of Classification Search
CPC ..... H01J 49/401; H01J 49/0031; H01J 49/004
USPC ........................ 250/281, 282, 283, 286, 287
See application file for complete search history.

(56) References Cited

U.S. PATENT DOCUMENTS

| 5,689,111 | A | 11/1997 | Dresch et al. |
| 6,621,074 | B1 | 9/2003 | Vestal |
| 6,900,430 | B2 | 5/2005 | Okumura et al. |
| 7,019,285 | B2 | 3/2006 | Dresch et al. |
| 7,038,197 | B2 | 5/2006 | Bateman et al. |
| 7,095,015 | B2 | 8/2006 | Bateman et al. |
| 7,385,187 | B2 | 6/2008 | Verentchikov |
| 7,683,314 | B2 | 3/2010 | Green et al. |
| 9,048,073 | B2 | 6/2015 | Bateman et al. |
| 9,129,781 | B2 * | 9/2015 | Richardson ......... H01J 49/0027 |
| 2007/0023635 | A1 | 2/2007 | Bateman et al. |
| 2008/0149825 | A1 | 6/2008 | Kozlovski et al. |
| 2010/0108879 | A1 | 5/2010 | Bateman et al. |

* cited by examiner

*Primary Examiner* — Nicole Ippolito
(74) *Attorney, Agent, or Firm* — Diederiks & Whitelaw, PLC

(57) ABSTRACT

A method of mass spectrometry is disclosed comprising separating ions according to one or more physico-chemical properties. Ions which are onwardly transmitted to a Time of Flight mass analyzer are controlled by attenuating ions which would otherwise be transmitted to the Time of Flight mass analyzer and cause saturation of an ion detector and which have been determined or which are predicted to have a relatively high intensity.

19 Claims, 7 Drawing Sheets

M/Z TARGETED ATTENUATION ON TIME OF FLIGHT INSTRUMENTS

CROSS-REFERENCE TO RELATED APPLICATIONS

This application is a continuation application of U.S. application Ser. No. 14/004,963, filed 13 Sep. 2013, which is the National Stage of International Application No. PCT/GB2012/050576, filed 15 Mar. 2012, which claims priority from and the benefit of U.S. Provisional Patent Application Ser. No. 61/452,772 filed on 15 Mar. 2011 and United Kingdom Patent Application No. 1104292.6 filed on 15 Mar. 2011. The entire contents of these applications are incorporated herein by reference.

BACKGROUND TO THE PRESENT INVENTION

This invention relates to apparatus and methods for improving the in-spectrum dynamic range of tandem Time of Flight ("TOF") mass spectrometers. Separation of ions prior to Time of Flight analysis has many existing applications.

According to a first example, ions may be separated by gas phase mobility (which in turn depends on shape and charge) allowing elucidation of structural information and/or removal of interference.

According to a second example, ions may be separated by mass to charge ratio (m/z) or mobility prior to fragmentation, reducing interference and improving confidence in assignment of fragment ions to precursor ions.

According to a third example, as packets of ions of equal energy produced by a travelling wave device travel into the pusher region of an orthogonal acceleration Time of Flight instrument, the constituent ions separate according to their mass to charge ratio. The timing of the Time of Flight pusher can be adjusted to allow enhancement in duty cycle optimised at chosen mass to charge ratios.

According to a fourth example, when the packets of ions described in the third example have been separated by ion mobility, it is possible to adjust the pusher synchronisation independently for each packet. Since mobility and mass to charge ratio are correlated, this results in an enhancement in duty cycle across the whole mass to charge ratio range.

The fourth example is an example of a High Duty Cycle (or "HDC") mode of operation of an orthogonal acceleration Time of Flight instrument. For the purposes of the present application, HDC operation entails at least one stage of separation and packetisation according to a physicochemical property that is correlated with mass to charge ratio and synchronisation of the orthogonal acceleration Time of Flight pusher to optimise transmission of a particular mass to charge ratio value for each packet.

In many applications, ions are accumulated prior to separation to avoid loss of sensitivity. When the effects of ion accumulation, separation and improved duty cycle are combined for any particular species, the maximum ion current observed at the ion detector can be increased substantially. For low abundance components this results in improvement in the limit of detection, quantification and mass measurement. However, for high abundance species, the resulting ion current can exceed the dynamic range of the ion detector to the detriment of mass measurement and quantification.

Known methods of attenuation of ion signals typically reduce the transmission of all ions to some extent.

It is desired to provide an improved mass spectrometer and method of mass spectrometry.

SUMMARY OF THE INVENTION

According to an aspect of the present invention there is provided a method of mass spectrometry comprising:
separating ions according to one or more physico-chemical properties;
providing a Time of Flight mass analyser; and
controlling ions which are onwardly transmitted to the Time of Flight mass analyser by attenuating first ions having a first physico-chemical property within one or more first ranges which would otherwise be transmitted to the Time of Flight mass analyser and which have been determined to have or which are predicted to have a relatively high intensity.

According to the preferred embodiment the first ions are attenuated if they are determined or predicted to cause saturation of other adverse affects to the ion detector.

The step of controlling ions which are onwardly transmitted to the Time of Flight mass analyser preferably further comprises attenuating first ions having a second physico-chemical property within one or more second ranges.

According to an embodiment a two dimensional or multidimensional separation is performed wherein ions are simultaneously separated according to two different physico-chemical properties (e.g. ion mobility and mass to charge ratio) and wherein first ions which are attenuated have both a first physico-chemical property (e.g. ion mobility) within one or more first (e.g. ion mobility) ranges and a second physico-chemical property (e.g. mass to charge ratio) within one or more second (e.g. mass to charge ratio) ranges.

According to another embodiment a plurality of one dimensional or single dimensional separations are performed in series or sequentially wherein ions are initially separated according to a first physico-chemical property (e.g. ion mobility or mass to charge ratio) and wherein first ions which are attenuated have a first physico-chemical property (e.g. ion mobility or mass to charge ratio) within one or more first (e.g. ion mobility or mass to charge ratio) ranges and wherein the ions are then subsequently separated according to a second physico-chemical property (e.g. ion mobility or mass to charge ratio) and wherein first ions which are attenuated have a second physico-chemical property (e.g. ion mobility or mass to charge ratio) within one or more second ranges.

The step of separating ions according to one or more physico-chemical properties preferably comprises separating ions according to their ion mobility.

The first ions which are attenuated preferably have ion mobilities within one or more first ion mobility ranges.

The step of separating ions according to one or more physico-chemical properties may less preferably comprise separating ions according to their mass or mass to charge ratio. According to this embodiment, the first ions which are attenuated preferably have masses or mass to charge ratios within one or more first mass or mass to charge ratio ranges.

The step of attenuating the first ions preferably comprises onwardly transmitting 0%, <10%, 10-20%, 20-30%, 30-40%, 40-50%, 50-60%, 60-70%, 70-80%, 80-90% or >90% of first ions having a physico-chemical property within the one or more first ranges.

The step of attenuating the first ions preferably comprises onwardly transmitting <10%, 10-20%, 20-30%, 30-40%, 40-50%, 50-60%, 60-70%, 70-80%, 80-90% or 90-100% of other ions having a physico-chemical property outside of the one or more first ranges. According to the preferred embodiment ions having a physico-chemical property outside the one or more first ranges are not substantially attenuated or less preferably are attenuated to a lesser degree.

First ions having a physico-chemical property within the one or more first ranges are preferably attenuated to a greater relative extent than other ions having a physico-chemical property outside of the one or more first ranges.

The step of controlling ions which are onwardly transmitted to the Time of Flight mass analyser preferably comprises controlling the timing at which an orthogonal acceleration pulse is applied to an orthogonal acceleration electrode into order to orthogonally accelerate ions into a time of flight region of the Time of Flight mass analyser. The timing of energising the orthogonal acceleration electrode is preferably arranged so that the first ions are not orthogonally accelerated and hence are lost to the system.

The step of controlling ions which are onwardly transmitted to the Time of Flight mass analyser may comprise controlling one or more ion optical lenses arranged upstream of the Time of Flight mass analyser.

The one or more ion optical lenses are preferably arranged and adapted to control the focusing or defocusing of an ion beam so that in a mode of operation a reduced intensity of ions is onwardly transmitted.

The step of controlling ions which are onwardly transmitted to said Time of Flight mass analyser may comprise repeatedly switching an ion attenuation device ON and OFF, wherein the duty cycle of the ion attenuation device may be varied in order to control the degree of attenuation of the ions.

The method may further comprise post-processing mass spectral data and/or a mass spectrum wherein the intensity of selected mass to charge ratio data and/or one or more mass or mass to charge ratio peaks is increased to correct for or compensate for the effect of attenuating the first ions.

According to another aspect of the present invention there is provided a mass spectrometer comprising:

a device arranged and adapted to separate ions according to one or more physico-chemical properties;

a Time of Flight mass analyser; and a control system arranged and adapted to control ions which are onwardly transmitted to the Time of Flight mass analyser by attenuating first ions having a first physico-chemical property within one or more first ranges which would otherwise be transmitted to the Time of Flight mass analyser and which have been determined to have or which are predicted to have a relatively high intensity.

According to the preferred embodiment the first ions are attenuated if they are determined or predicted to cause saturation of other adverse affects to the ion detector.

According to an aspect of the present invention there is provided a mass spectrometer comprising:

one or more separation devices capable of separating ions according to one or more of their physicochemical properties;

one or more signal attenuation devices operating on a timescale shorter than the range of separation times afforded by the one or more separation devices;

a Time of Flight mass spectrometer; and a means of or device for controlling each signal attenuation device so that one or more selected regions of the available separation space is targeted for attenuation.

According to an aspect of the present invention there is provided a method of mass spectrometry comprising:

separating ions according to one or more of their physicochemical properties;

providing one or more signal attenuation devices operating on a timescale shorter than the range of separation times afforded by the one or more separation devices;

providing a Time of Flight mass spectrometer; and controlling each signal attenuation device so that one or more selected regions of the available separation space is targeted for attenuation.

The present invention addresses the lack of specificity of attenuation of conventional methods.

The preferred embodiment is possible when ions to be injected into a Time of Flight mass analyser are subjected to preliminary separation by any one of (or a combination of) a variety of physical characteristics C, C', C" . . . on a timescale that is longer than that associated with Time of Flight analysis. It is then possible to employ a variety of signal attenuation methods operating on a shorter timescale than the fastest separation to selectively suppress signal for analytes with C, C', C" . . . near to one or more sets of target values $C_i$, $C'_i$, $C''_i$ . . . without reducing the detected signal for components outside the targeted ranges. Alternatively, when a nested multidimensional separation is not available, separation and attenuation in each dimension may be performed sequentially. This may require the use of more than one attenuation device. For example, the following steps may be performed: (i) separation according to some physicochemical characteristic C; (ii) attenuation near one or more target values $C_i$; (iii) separation according to some physicochemical characteristic C'; (iv) attenuation near one or more target values $C'_i$ and so on. This will result in some attenuation outside the targeted ranges in each dimension, but regions where the one dimensional ranges overlap will be attenuated most.

The specificity of the attenuation is preferably determined by the quality of the preliminary separations and the speed of the attenuation mechanism. If the attenuation method is quantitative, then data in the affected range may be rescaled appropriately for display and/or data analysis. In a feedback mode of operation, where the composition of the analyte is changing with time, the range to target may be determined automatically using data already collected.

In a preferred embodiment of the present invention, the method comprises an ion source upstream of a series of accumulation, separation and attenuation devices and a Time of Flight analyser. At least one separation device and one attenuation device is required.

A preferred mode of operation is as follows.

Firstly, ions enter from the ion source and pass into an accumulating device.

Secondly, after a period of accumulation, a packet of ions is released into a separation device. Any particular species will emerge from the separation device according to some probability distribution $Pr(T_{SEP}$ GIVEN C) where $T_{SEP}$ is the time taken to pass through the separation device and C is some physicochemical characteristic (or combination of physicochemical characteristics) of the ions.

Thirdly, ions then pass through a device that has transmission which can be controlled on a timescale that is shorter than the range of observed separation times, allowing transmission of ions to be correlated with their separation time. Transmission is reduced at times close to $T^*_{SEP}(C_i)$ where the $C_i$ are characteristic of one or more species targeted for attenuation.

Fourthly, in an optional feedback mode, the values $C_i$ chosen for attenuation are adjusted with time as the composition of the sample entering the instrument changes.

Fifthly, finally the transmitted ions pass into the Time of Flight analyser for mass measurement.

Possible useful physicochemical characteristics C include, but are not limited to, mass to charge ratio, mass, charge and gas phase ion mobility.

Some examples of separation devices include ion mobility cells, ion traps and scanwave wherein the height of a DC and/or pseudo-potential barrier within an ion trap is progressively varied so that ions emerge from the ion trap in order or reverse order of their mass to charge ratio.

According to the preferred embodiment the attenuation device is controlled on a timescale $T_{ATT}$ that is small or short enough to preserve a useful correlation between the physicochemical characteristic C and the transmission ratio. In one embodiment the distribution $Pr(T_{SEP}$ GIVEN C) may be peaked near a characteristic time $T^*_{SEP}(C)$ with a peak width given by $\Delta T(C)$. If $T_{ATT} < \Delta T(C)$ then the specificity of attenuation will be limited by the width $\Delta T(C)$ of the separation device. In this case, reducing $\Delta T(C)$ will result in improved specificity of attenuation.

According to an aspect of the present invention there is provided a mass spectrometer comprising:

one or more separation devices capable of separating ions according to their physicochemical properties;

one or more signal attenuation devices operating on a timescale shorter than the range of separation times afforded by the one or more separation devices;

a Time of Flight mass spectrometer; and a means of or device for controlling each attenuation device so that one or more selected regions of the available separation space is targeted for attenuation.

The Time of Flight mass spectrometer preferably comprises an orthogonal acceleration Time of Flight mass spectrometer.

According to an embodiment one or more targeted regions are chosen in such a way that selected molecular species that have been detected previously are attenuated.

One or more of the separation devices may be preceded by an accumulation device.

One or more of the separation devices may separate by mass to charge ratio.

One or more of the separation devices may separate by ion mobility.

One of the separation devices may comprises a travelling wave ion mobility cell wherein one or more transient DC voltages or potentials are applied to the electrodes of an ion mobility cell in order to cause ions to separate according to their ion mobility.

One or more of the separation devices may comprise a step wave device comprising an ion guide having two ion paths wherein ions are switched from a first ion path to a second different ion path. The ion guide may, for example, comprise a plurality of electrodes having apertures wherein at least some of the electrodes comprise conjoined electrodes.

One or more of the separation devices preferably comprises an ion trap.

According to an embodiment one of the attenuation devices may comprise a Dynamic Range Enhancement ("DRE") lens.

One of the attenuation devices preferably comprises the ion optics which are used to transfer ions into the pusher region of an orthogonal acceleration Time of Flight mass spectrometer.

One separation device may comprise the pusher region of an orthogonal acceleration Time of Flight mass spectrometer.

One of the attenuation devices may comprise the pusher region of an orthogonal acceleration Time of Flight mass spectrometer.

The mass spectrometer is preferably operated in a High Duty Cycle ("HDC") mode of operation.

The High Duty Cycle ("HDC") calibration is preferably modified to attenuate one or more targeted regions in ion mobility and mass to charge ratio space.

The High Duty Cycle ("HDC") calibration is preferably adaptively modified to reflect the composition of previously detected species entering the mass spectrometer.

The High Duty Cycle ("HDC") calibration preferably switches among two or more alternative paths.

The degree of attenuation is preferably recorded in a form that permits approximate reconstruction of the signal that would have been observed in the absence of attenuation.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) one or more energy analysers or electrostatic energy analysers; and/or (h) one or more ion detectors; and/or (i) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (j) a device or ion gate for pulsing ions; and/or (k) a device for converting a substantially continuous ion beam into a pulsed ion beam.

The mass spectrometer may further comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

An ion mobility spectrometer according to the preferred embodiment may comprise a plurality of electrodes each having an aperture through which ions are transmitted in use. One or more transient DC voltages or potentials or one or more DC voltage or potential waveforms may be applied to the electrodes comprising the ion mobility spectrometer in order to urge ions along the length of the ion mobility spectrometer.

According to the preferred embodiment the one or more transient DC voltages or potentials or the one or more DC voltage or potential waveforms create: (i) a potential hill or barrier; (ii) a potential well; (iii) multiple potential hills or barriers; (iv) multiple potential wells; (v) a combination of a potential hill or barrier and a potential well; or (vi) a combination of multiple potential hills or barriers and multiple potential wells.

The one or more transient DC voltage or potential waveforms preferably comprise a repeating waveform or square wave.

An RF voltage is preferably applied to the electrodes of the ion mobility spectrometer and preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; (xi) 500-550 V peak to peak; (xxii) 550-600 V peak to peak; (xxiii) 600-650 V peak to peak; (xxiv) 650-700 V peak to peak; (xxv) 700-750 V peak to peak; (xxvi) 750-800 V peak to peak; (xxvii) 800-850 V peak to peak; (xxviii) 850-900 V peak to peak; (xxix) 900-950 V peak to peak; (xxx) 950-1000 V peak to peak; and (xxxi) >1000 V peak to peak.

The RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The ion mobility spectrometer is preferably maintained at a pressure selected from the group comprising: (i) >0.001 mbar; (ii) >0.01 mbar; (iii) >0.1 mbar; (iv) >1 mbar; (v) >10 mbar; (vi) >100 mbar; (vii) 0.001-0.01 mbar; (viii) 0.01-0.1 mbar; (ix) 0.1-1 mbar; (x) 1-10 mbar; and (xi) 10-100 mbar.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

A preferred embodiment of the present invention will now be described.

Figure 1:
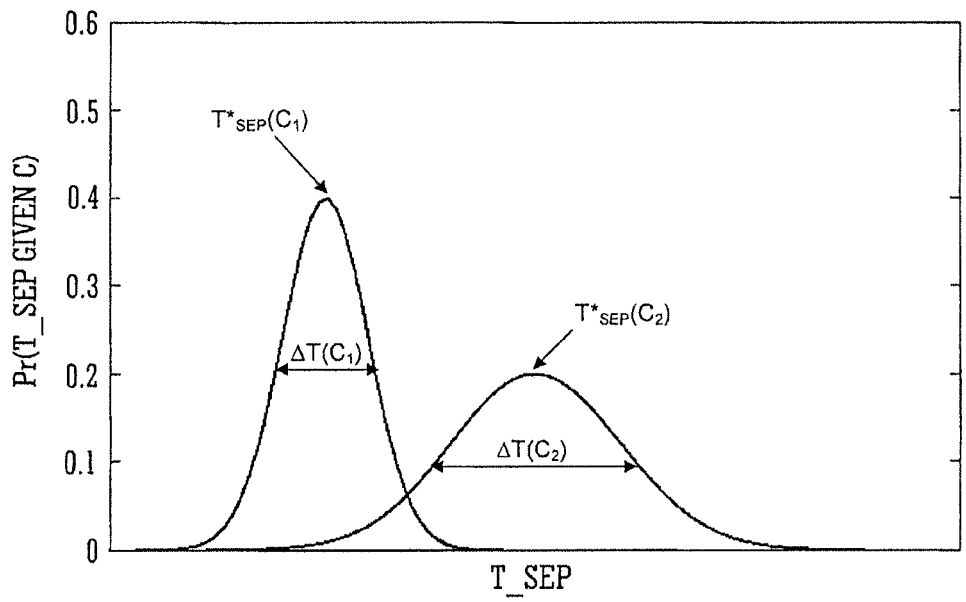
FIG. 1 shows probability distributions for two different species.

FIG. 1 shows probability distributions $T_{SEP}$ of two different ion species showing different characteristic times and separation widths. Both distributions have been normalised to have unit area. A signal attenuation device may be utilised during the time period $T^*_{SEP}(C_1) +/- \frac{1}{2}\Delta T(C_1)$ with the result that ion species #1 will be suppressed relative to ion species #2. Note that in this case some reduction of the signal for ion species #2 will also be observed due to the overlap of the two distributions. This effect disappears with improving separation (i.e. smaller peak widths ΔT).

The separation device may be replaced by a series of separation devices operating on ever shorter timescales, resulting in a nested multidimensional separation. This results in extra specificity so long as the attenuation device is operated on the timescale of the fastest (and final) separation.

Figure 2:
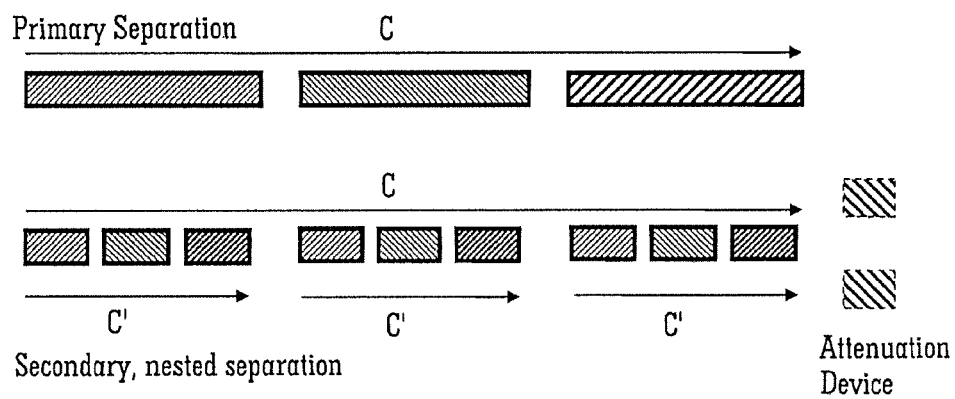
FIG. 2 illustrates an embodiment wherein a nested two dimensional separation based on physiochemical properties has been carried out.
Figure 3:
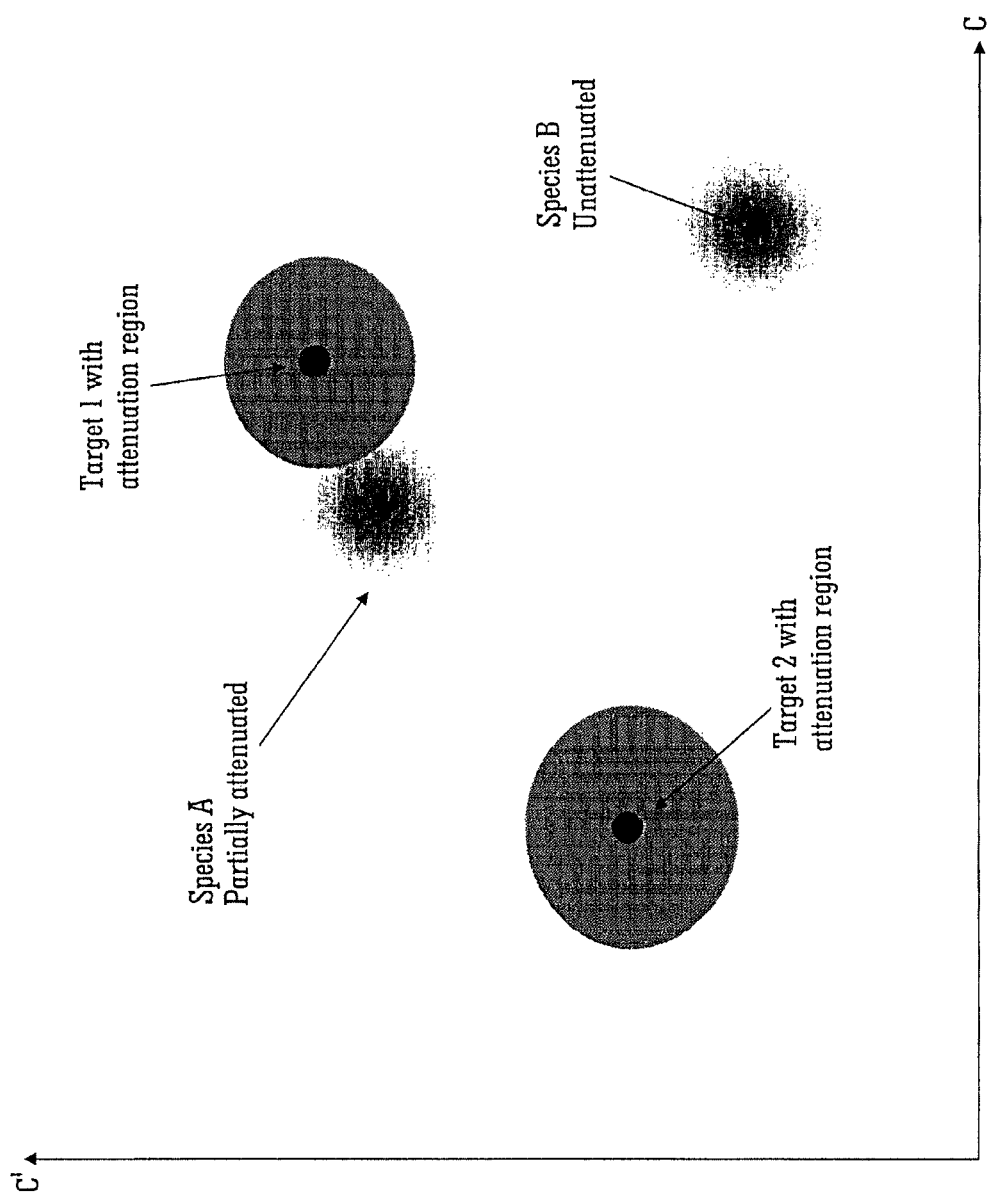
FIG. 3 shows targets with attenuation regions.

FIG. 2 illustrates an embodiment of the present invention in which a nested two dimensional separation based on physiochemical characteristics C and C' has been carried out. After the second phase of separation, ions are in packets that can be labelled by both C and C' and it is possible to target packets with particular values of C and C' for attenuation. This is further illustrated in FIG. 3. FIG. 3 shows points in black which have been targeted. According to the preferred embodiment attenuation is carried out in the regions defined by the solid grey areas or ellipses. Species with separation profiles overlapping the solid grey ellipses such as Species A will be attenuated to some extent while other species such as Species B will be unaffected.

According to various embodiments different attenuation devices may be used. For example, a Dynamic Range Enhancement ("DRE") lens may be used. Alternatively, the ion optics used to manipulate ions as they move into a pusher region of a Time of Flight mass analyser and the pusher region itself may be used wherein the timing of individual pushes can be controlled with sufficient accuracy.

Attenuation may be performed between separation devices in which case it is not required that the corresponding separation timescales are nested.

A single physical device may serve more than one of the purposes listed above. For example, a travelling wave ion mobility separation device may packetize ions in a form suitable for subsequent separation. Similarly, a Time of Flight pusher can simultaneously act as a mass to charge ratio separation and attenuation device.

Figure 4:
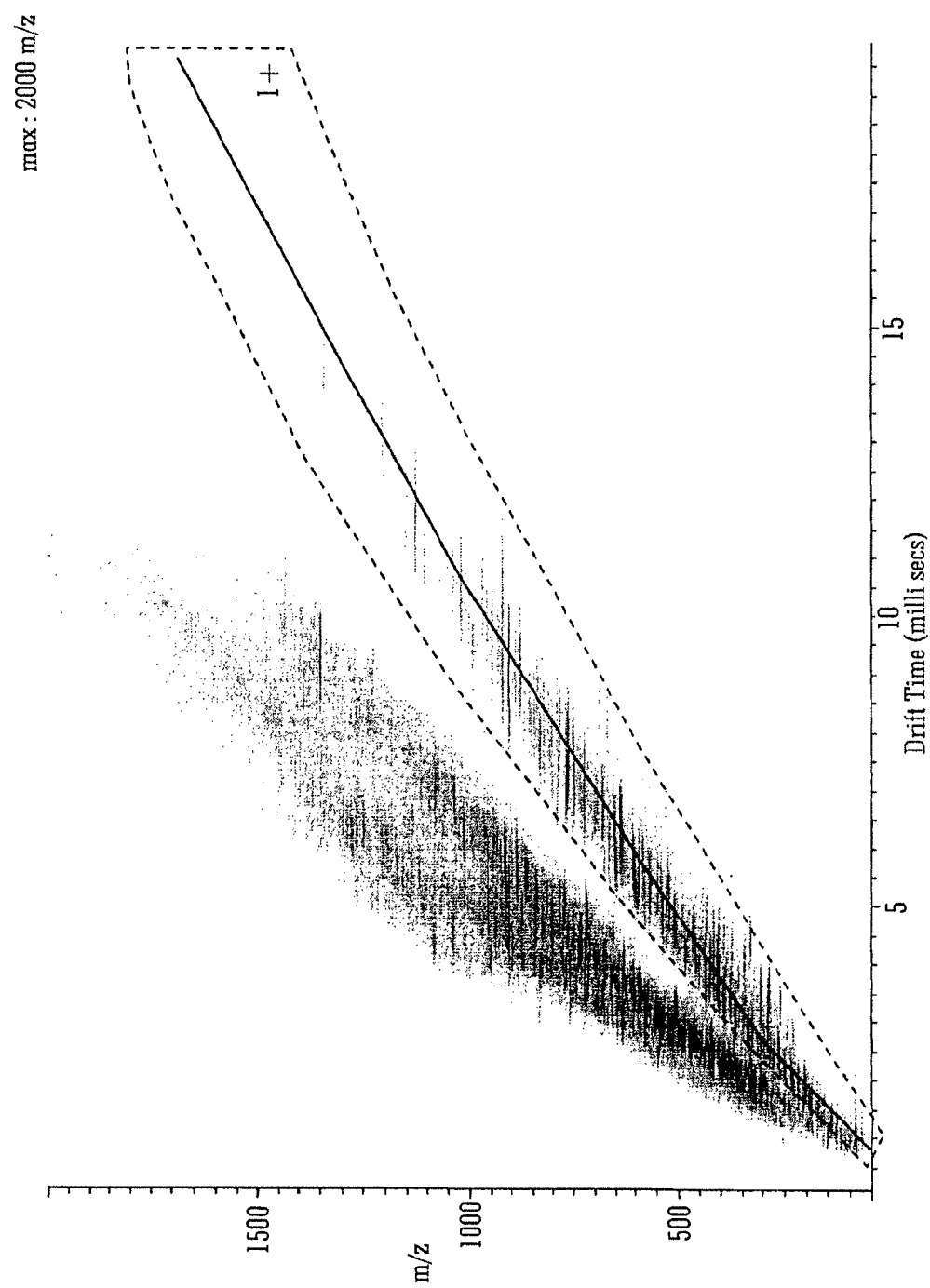
FIG. 4 illustrates a targeted attenuation mode.

In one mode of operation of the preferred embodiment, a hybrid Ion Mobility Spectrometry ("IMS") Time of Flight ("TOF") instrument may be operated in a High Duty Cycle ("HDC") mode. In this mode the timing of energising the pusher electrode is adjusted to maximise transmission at a particular mass to charge ratio for packets of a given ion mobility. In normal operation, the mass to charge ratios are chosen to lie along a path in mobility and mass to charge ratio space which allows, for example, optimisation of transmission for a selected charge state. Such a path is known as an High Duty Cycle ("HDC") calibration. This situation is illustrated in FIG. 4 in which the mass to charge ratio that would be chosen for a packet of ions having a given mobility is defined by the black line. The High Duty Cycle ("HDC") calibration in the figure has been selected for optimisation of transmission of singly charged (1+) species which lie predominantly in the region inside the dashed line.

Figure 5:
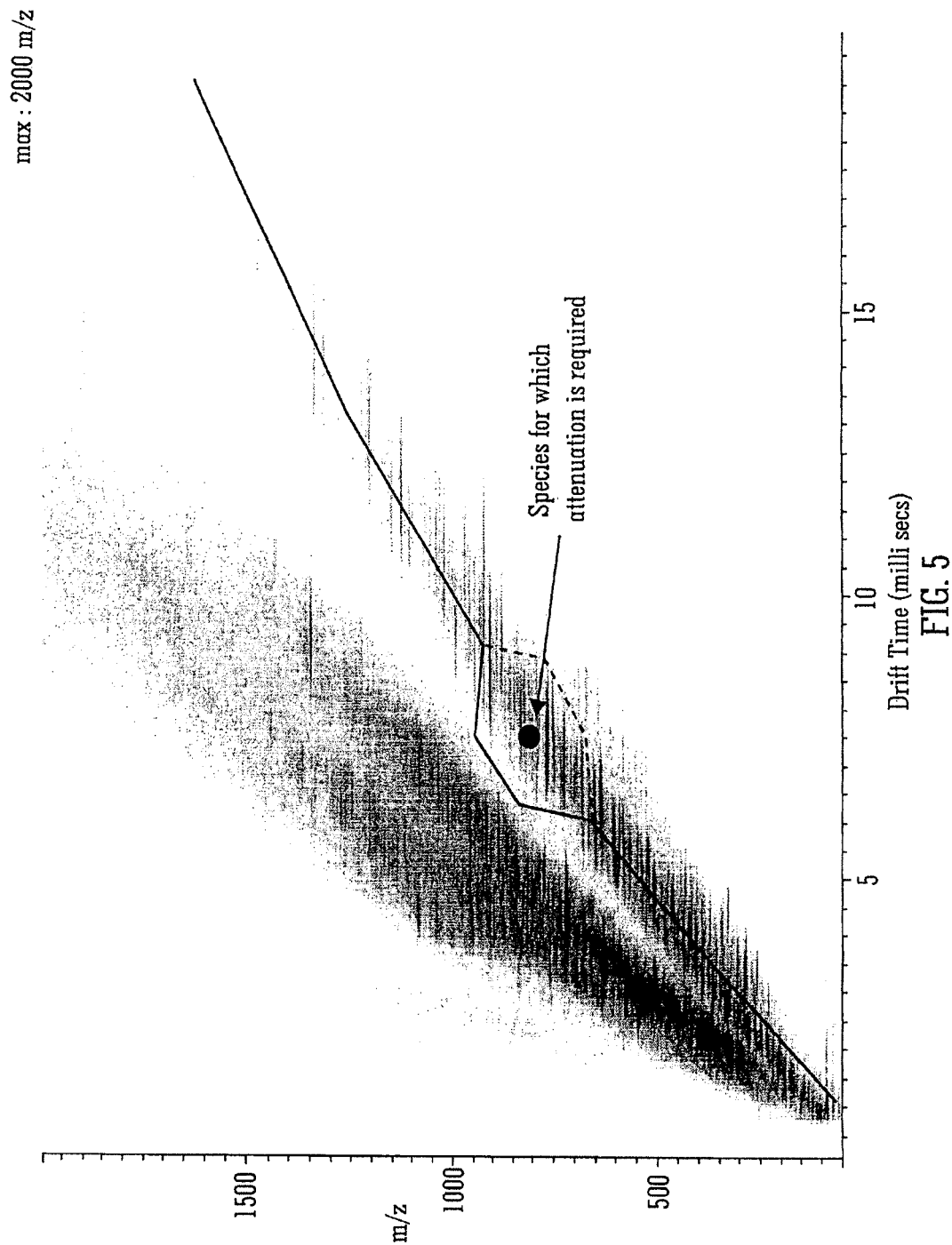
FIG. 5 illustrates an intense ion species which is desired to be attenuated in order to avoid detector saturation in accordance with an embodiment of the present invention.

A targeted attenuation mode is shown in FIG. 5 in which two alternative calibrations result in attenuation of a singly charged signal in the vicinity of a species with mass and mobility defined by a large black dot. The calibrations coincide except in the vicinity of the black dot where they diverge to pass the species of interest on opposite sides. Many other calibrations are possible, and it is sometimes beneficial to switch between several different calibrations. Note that factors used to determine the size of the detour include the quality of the separation and the degree of attenuation required.

In an optional feedback mode of operation, the paths chosen may change with time to adapt to the composition of the sample currently entering the instrument. According to an embodiment calibration paths may detour to avoid several species. Many attenuation devices are at least partially quantitative in the sense that the degree of attenuation is at least approximately known. When such a device is used then it is beneficial to record the degree of attenuation used so that the underlying (unattenuated) signal can be at least approximately reconstructed.

Figure 6A:
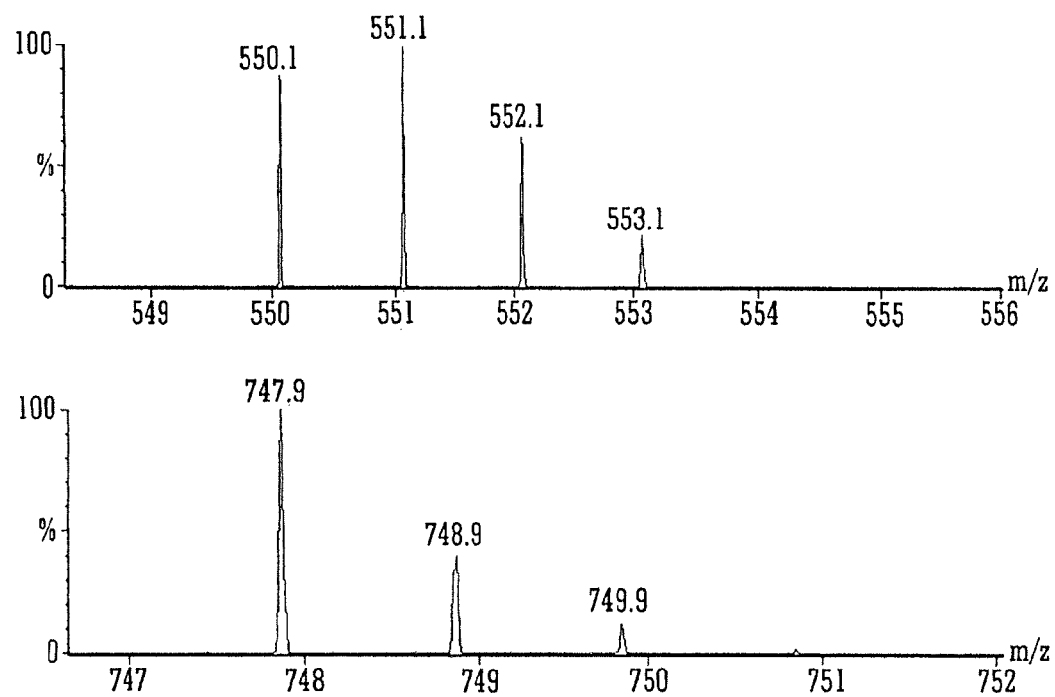
FIG. 6A shows simulated TDC spectra for two analytes.
Figure 6B:
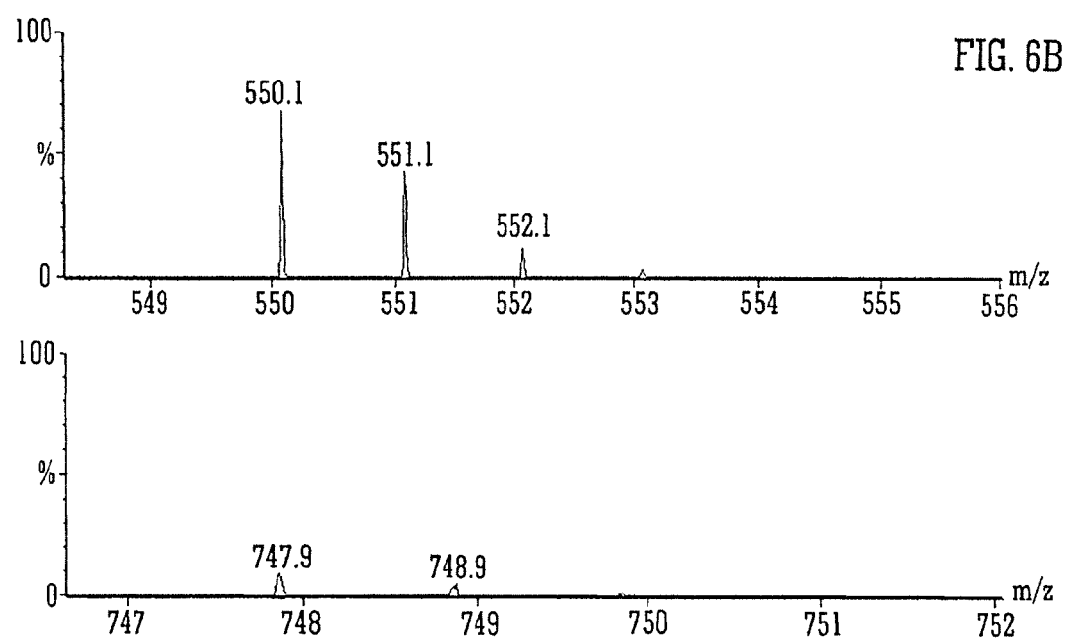
FIG. 6B shows simulated TDC spectra for the two analytes wherein the signal for both analytes has been reduced by a factor of ×10 and FIG. 6C illustrates an embodiment of the present invention wherein one analyte has been attenuated whereas the other analyte is unattenuated.
Figure 6C:
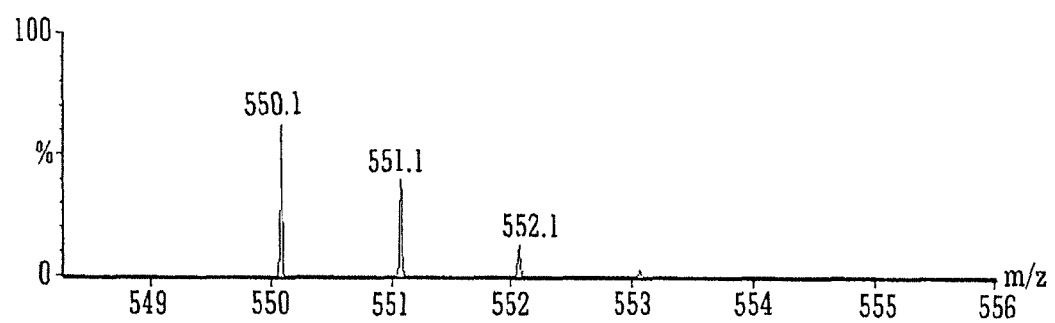
Figure 6C:
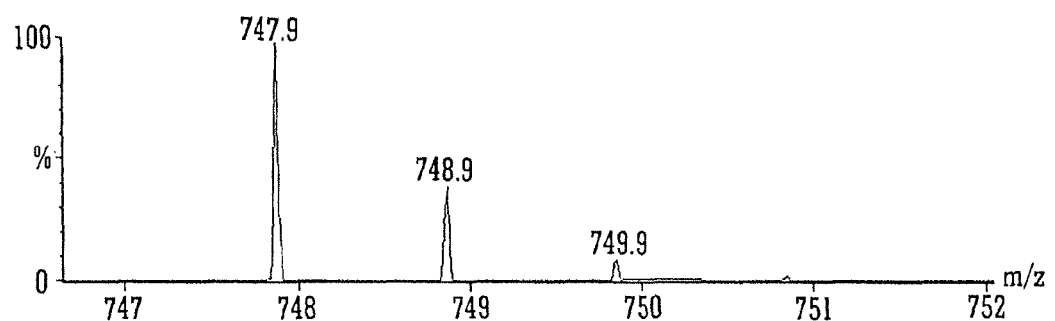

FIGS. 6A-6C show three simulated TDC spectra for two analytes. The first analyte A has a mass to charge ratio of 550 and the second analyte B has a mass to charge ratio of 748. The two analytes A,B have Electrospray MS responses which differ by a factor of $10^3$.

In FIG. 6A no attenuation is used, and the isotope distribution of analyte A is severely distorted by detector lead-time.

In FIG. 6B an attenuation device has been employed to reduce the signal for both analytes A,B by a factor of ×10. This has improved the isotope distribution for species A, but species B is now so weak that its final isotope is no longer visible.

FIG. 6C illustrates an embodiment of the present invention wherein species A has been targeted for attenuation by a factor of ×10 whilst species B is unaffected or unattenuated. This degree of specificity is achievable on current IMS-TOF instruments. The entire isotope distributions of both species are now recorded faithfully.

FIGS. 7A-E illustrate attenuation according to an embodiment of the present invention wherein an IMS-TOF mass spectrometer is operated in a HDC acquisition mode.

Figures 7A, 7B, 7C, 7D, 7E:
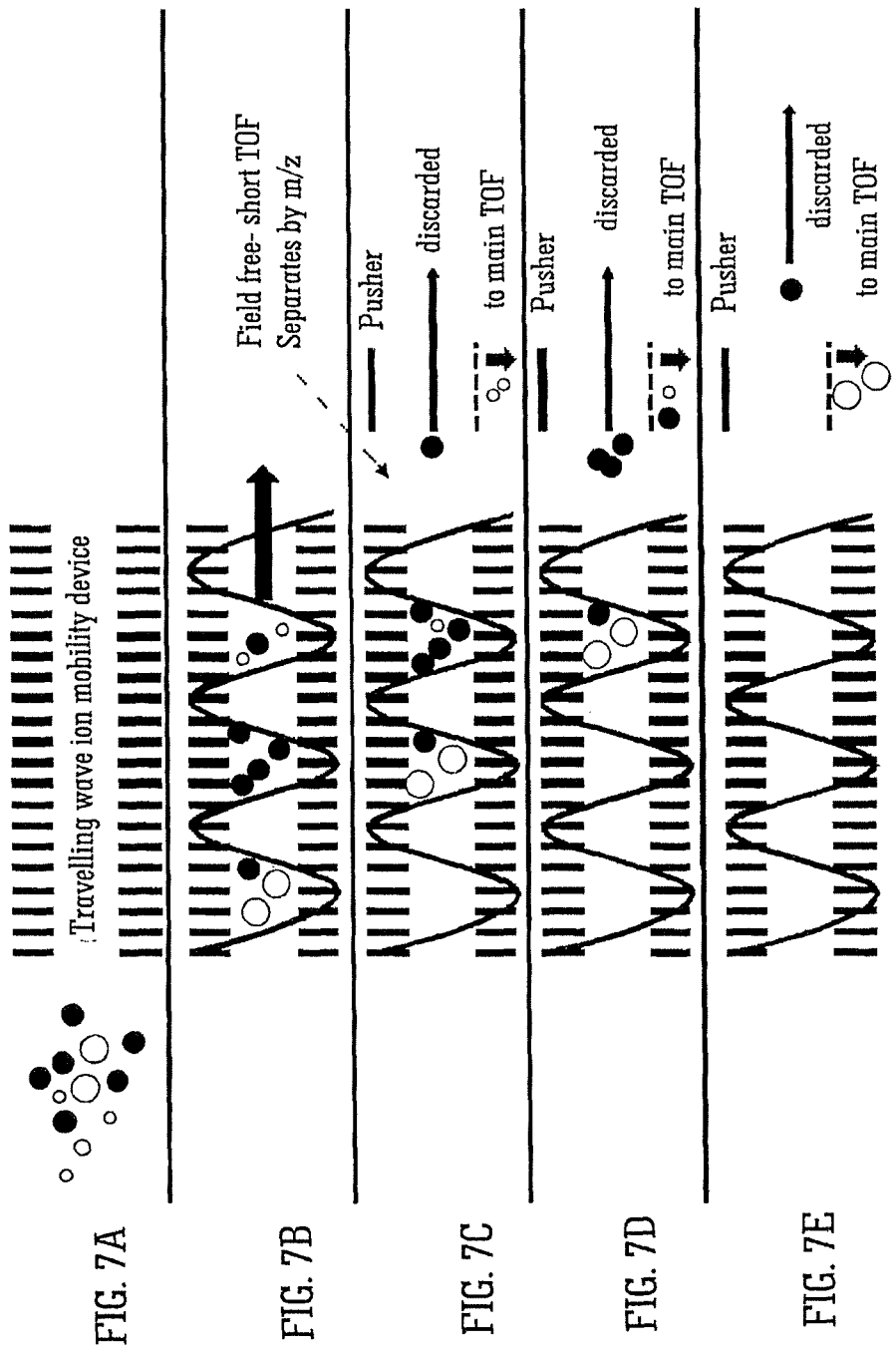
FIG. 7A illustrates attenuation in a High Duty Cycle acquisition mode of operation of an IMS-Time of Flight mass spectrometer and shows a mixed population of ions trapped in preparation for ion mobility separation.
FIG. 7B shows the ions separated according to their ion mobility.
FIG. 7C shows the first ion packet having exited the ion mobility device.
FIG. 7D shows the second ion packet having been released from the ion mobility device and FIG. 7E shows the third ion packet having been released into the pusher region.

FIG. 7A shows a mixed population of ions trapped in preparation for ion mobility separation. Three species are present. The species in black (with intermediate mass to charge ratio and ion mobility) is of relatively high abundance and attenuation of this species is desired in order to prevent saturation of the ion detector.

FIG. 7B shows ions which have been separated into packets according to ion mobility. The rightmost packet contains mainly the smallest ions having the highest mobility. The central packet contains a mixture of small ions and intermediate mobility ions. The final packet contains intermediate and low mobility ions.

After ions leave the ion mobility device, each packet passes into a field free i.e. a short time of flight region in which the constituent ions begin to separate by mass to charge ratio. The timing of a pusher pulse applied to a pusher electrode is preferably adjusted such that, for each packet, ions in a particular mass to charge ratio range are preferentially pushed into the main time of flight region of the Time of Flight mass analyser. The variation of pusher timing with mobility separation time is referred to as the HDC calibration.

As shown in FIG. 7C, the first ion packet has exited the ion mobility device. The small ions have a lower mass to charge ratio than the ions of intermediate size and enter the pusher region first. The pusher pulse has been timed so that the small (and low mass to charge ratio) ions are pushed downwards into the main Time of Flight region, while the intermediate (in size and mobility) ions pass straight through the pusher region and are subsequently discarded.

In FIG. 7D, the second packet has been released from the ion mobility device and the pusher timing has been adjusted such that the small (low mass to charge ratio) ions and only a small fraction of the intermediate ions are pushed into the main Time of Flight region.

In FIG. 7E, the third packet has been released into the pusher region. In this case, the pusher has been timed to transmit the large ions and discard the ions of intermediate size and mass to charge ratio.

According to an embodiment the species or regions to be targeted for attenuation may be identified using data already collected in the same experiment. For example, during an LC-MS experiment in which more than one spectrum is acquired during the elution of a chromatographic peak, it is possible to identify (in real time) species with high or rising intensities and to target these for attenuation. Alternatively, data may be acquired specifically for the purpose of determining attenuation regions. For example, short "pre-scan" acquisitions may be inserted to identify highly abundant species to target for attenuation. This pre-scan data may be retained for diagnostic purposes, or simply discarded.

Although the present invention has been described with reference to the preferred embodiments, it will be understood by those skilled in the art that various changes in form and detail may be made without departing from the scope of the invention as set forth in the accompanying claims.

The invention claimed is:

1. A method of mass spectrometry conducted with a Time of Flight mass analyser including an ion detector, said method comprising:
controlling ions which are transmitted to said Time of Flight mass analyser by attenuating first ions having a first physico-chemical property and a second physico-chemical property within one or more targeted attenuation regions which would otherwise be transmitted to said Time of Flight mass analyser and which have been determined to have or which are predicted to have a relatively high intensity such as to cause saturation of said ion detector.

2. A method as claimed in claim 1, wherein a two dimensional or multidimensional separation is performed wherein ions are simultaneously separated according to said first and second physico-chemical properties and wherein first ions which are attenuated have both a first physico-chemical property within one or more first ranges and a second physico-chemical property within one or more second ranges.

3. A method as claimed in claim 1, wherein a plurality of one dimensional or single dimensional separations are performed in series or sequentially wherein ions are initially separated according to said first physico-chemical property and wherein first ions which are attenuated have a first physico-chemical property within one or more first ranges and wherein said ions are then subsequently separated according to said second physico-chemical property and wherein first ions which are attenuated have a second physico-chemical property within one or more second ranges.

4. A method as claimed in claim 1, wherein said step of attenuating said first ions comprises onwardly transmitting 0%, <10%, 10-20%, 20-30%, 30-40%, 40-50%, 50-60%, 60-70%, 70-80%, 80-90% or >90% of first ions having a first physico-chemical property within one or more first ranges.

5. A method as claimed in claim 1, wherein said step of attenuating said first ions comprises onwardly transmitting <10%, 10-20%, 20-30%, 30-40%, 40-50%, 50-60%, 60-70%, 70-80%, 80-90% or 90-100% of other ions having a first physico-chemical property outside of one or more first ranges.

6. A method as claimed in claim 1, wherein said first ions having a first physico-chemical property within one or more first ranges are attenuated to a greater relative extent than other ions having a first physico-chemical property outside of said one or more first ranges.

7. A method as claimed in claim 1, wherein said step of controlling ions which are onwardly transmitted to said Time of Flight mass analyser comprises controlling the timing at which an orthogonal acceleration pulse is applied to an orthogonal acceleration electrode in order to orthogonally accelerate ions into a time of flight region of said Time of Flight mass analyser.

8. A method as claimed in claim 1, wherein said step of controlling ions which are onwardly transmitted to said Time of Flight mass analyser comprises controlling one or more ion optical lenses arranged upstream of said Time of Flight mass analyser.

9. A method as claimed in claim 8, wherein said one or more ion optical lenses are arranged and adapted to control the focusing or defocusing of an ion beam so that in a mode of operation a reduced intensity of ions is onwardly transmitted.

10. A method as claimed in claim 1, wherein said step of controlling ions which are onwardly transmitted to said Time of Flight mass analyser comprises repeatedly switching an ion attenuation device ON and OFF, wherein the duty cycle of said ion attenuation device may be varied in order to control the degree of attenuation of said ions.

11. A method as claimed in claim 1, further comprising post-processing mass spectral data or a mass spectrum wherein the intensity of selected mass or mass to charge ratio data or one or more mass or mass to charge ratio peaks is increased to correct for or compensate for the effect of attenuating said first ions.

12. A method as claimed in claim 1, wherein said first physico-chemical property or said second physico-chemical property is selected from the group consisting of: ion mobility; gas phase ion mobility; charge; mass to charge ratio; and mass.

13. A method as claimed in claim 1, wherein said first physico-chemical property is different from said second physico-chemical property.

14. A method as claimed in claim 1, wherein said step of attenuating said first ions comprises attenuating said first ions having a first physico-chemical property within one or more first ranges and a second physico-chemical property within one or more second ranges.

15. A method as claimed in claim 1, further comprising a step of determining said first ions that have or are predicted to have a relatively high intensity such as to cause saturation of said ion detector.

16. A method as claimed in claim 1, wherein said one or more targeted attenuation regions are regions of a separation space.

17. A method as claimed in claim 16, wherein said separation space is two dimensional or multidimensional.

18. A method as claimed in claim 1, wherein said one or more targeted attenuation regions are substantially elliptical.

19. A mass spectrometer comprising:
a Time of Flight mass analyser including an ion detector; and
a control system arranged and adapted to control ions which are transmitted to said Time of Flight mass analyser by attenuating first ions having a first physico-chemical property and a second physico-chemical property within one or more targeted attenuation regions which would otherwise be transmitted to said Time of Flight mass analyser and which have been determined to have or which are predicted to have a relatively high intensity such as to cause saturation of said ion detector.

* * * * *